United States Patent [19]

Reime

[11] Patent Number: 5,666,037

[45] Date of Patent: Sep. 9, 1997

[54] ARRANGEMENT FOR MEASURING OR DETECTING A CHANGE IN A RETRO-REFLECTIVE ELEMENT

[76] Inventor: Gerd Reime, Friedenstr. 88, D-75328 Schömberg, Germany

[21] Appl. No.: 578,685

[22] PCT Filed: Jun. 18, 1994

[86] PCT No.: PCT/DE94/00714

§ 371 Date: Apr. 15, 1996

§ 102(e) Date: Apr. 15, 1996

[87] PCT Pub. No.: WO95/01561

PCT Pub. Date: Jan. 12, 1995

[30] Foreign Application Priority Data

| Jul. 2, 1993 | [DE] | Germany | 93 09 837 U |
| Nov. 19, 1993 | [DE] | Germany | 43 39 572.4 |
| Nov. 19, 1993 | [DE] | Germany | 43 39 574.0 |
| Feb. 3, 1994 | [DE] | Germany | 44 03 221 |

[51] Int. Cl.$^6$ .................. G01J 5/02; H02H 7/08; A47L 1/00

[52] U.S. Cl. .................. 318/483; 318/DIG. 2; 15/250.001; 356/345; 356/361; 250/339.1

[58] Field of Search .................. 318/DIG. 2, 483, 318/443, 480, 444; 15/250.002, 250.001; 356/369, 239, 364, 361, 124, 152.1, 345; 250/339.1, 393

[56] References Cited

U.S. PATENT DOCUMENTS

| 4,378,168 | 3/1983 | Kuisma et al. ............... 73/599 |
| 4,542,325 | 9/1985 | Kobayashi et al. . |
| 4,620,141 | 10/1986 | McCumber et al. . |
| 4,916,374 | 4/1990 | Schierbeek et al. . |
| 4,960,996 | 10/1990 | Hochstein . |
| 5,082,629 | 1/1992 | Burgess, Jr. et al. ........ 356/128 |
| 5,436,541 | 7/1995 | Mangler et al. ............. 318/483 |
| 5,483,346 | 1/1996 | Butzer ......................... 356/369 |

FOREIGN PATENT DOCUMENTS

| 0 249 031 | 12/1987 | European Pat. Off. . |
| 0 408 304 | 1/1991 | European Pat. Off. . |
| 0 438 633 | 7/1991 | European Pat. Off. . |
| 0 520 302 | 12/1992 | European Pat. Off. . |
| 0 547 337 | 6/1993 | European Pat. Off. . |
| 0 562 275 | 9/1993 | European Pat. Off. . |
| 2 200 878 | 8/1973 | Germany . |
| 25 29 866 | 2/1976 | Germany . |
| 23 54 100 | 10/1976 | Germany . |
| 26 30 470 | 1/1978 | Germany . |

(List continued on next page.)

*Primary Examiner*—John W. Cabeca
*Attorney, Agent, or Firm*—Spencer & Frank

[57] ABSTRACT

An arrangement for indicating a change in a reflective element of a radiation-permeable medium having a detection side disposed opposite the reflective element. The arrangement includes two measured sections each having a radiation source for generating radiation for transmission through the radiation-permeable medium; a sensor-active surface on the reflective element for reflecting at least a portion of the generated radiation through the detection side; and a radiation receiver for receiving the reflected radiation which has an output for producing a detection signal representing received radiation. The arrangement further includes a switch arrangement for periodically actuating respective ones of the measured sections in a successive, repeating switching sequence according to a predetermined frequency; an adjusting device for adjusting the detection signal so that, in a rest state of the sensor-active surface of each measured section, a part of the detection signal corresponding to each measured section has an average amplitude value equal to an average amplitude value of parts of the detection signal corresponding to other ones of the measured sections; a filter circuit for producing a filtered detection signal; and an evaluation device having an input for receiving the filtered detection signal and producing an output signal in dependence of a difference between parts of the filtered detection signal corresponding to respective ones of the measured sections.

13 Claims, 10 Drawing Sheets

FOREIGN PATENT DOCUMENTS

| | | |
|---|---|---|
| 28 36 734 | 7/1979 | Germany . |
| 30 38 141 | 2/1982 | Germany . |
| 82 02 355 | 3/1983 | Germany . |
| 31 40 865 | 5/1983 | Germany . |
| 32 03 091 | 8/1983 | Germany . |
| 32 18 279 | 11/1983 | Germany . |
| 32 35 590 | 3/1984 | Germany . |
| 33 14 770 | 11/1987 | Germany . |
| 37 15 798 | 1/1988 | Germany . |
| 38 25 663 | 2/1989 | Germany . |
| 38 25 665 | 2/1989 | Germany . |
| 37 33 762 | 4/1989 | Germany . |
| 38 00 327 | 7/1989 | Germany . |
| 39 41 905 | 6/1990 | Germany . |
| 90 10 998 | 12/1990 | Germany . |
| 39 35 807 | 5/1991 | Germany . |
| 40 27 367 | 7/1991 | Germany . |
| 41 02 146 | 9/1991 | Germany . |
| 40 36 407 | 5/1992 | Germany . |
| 40 18 903 | 10/1992 | Germany . |
| 42 29 491 | 1/1993 | Germany . |
| 41 34 432 | 4/1993 | Germany . |
| 41 41 348 | 6/1993 | Germany . |
| 41 20 750 | 7/1993 | Germany . |
| 37 22 510 | 9/1993 | Germany . |
| 93 09 837 | 10/1993 | Germany . |
| 42 17 390 | 12/1993 | Germany . |
| 42 17 391 | 12/1993 | Germany . |
| 42 31 763 | 3/1994 | Germany . |
| 61-11637 | 1/1986 | Japan . |
| 90/08680 | 8/1990 | WIPO . |
| 91/09756 | 7/1991 | WIPO . |

ARRANGEMENT FOR MEASURING OR DETECTING A CHANGE IN A RETRO-REFLECTIVE ELEMENT

FIELD OF THE INVENTION

The invention relates to an arrangement for detecting or measuring a change in a reflective element which is part of a medium adapted to be penetrated by a predetermined radiation.

BACKGROUND OF THE INVENTION

In many instances, it is desirable to detect changes in a reflective element. Such changes are caused for example by a particular wetting of a surface, effected in order to derive control commands for closing windows or other openings for example, or for removing an interfering wetting. For example, an inner reflection surface of a radiation-permeable plate or wall (inner or total reflection), a mirror, or any other means, which possibly also reflects only stray light, can be considered as a reflecting element, such as, for example, a hand approaching the arrangement. The term wetting of a surface is understood to mean the covering or sprinkling of the surface with individual drops of liquid or the striking of drops of liquid against the surface, until a liquid film or foam is deposited on the surface, or until a liquid layer of a particular layer thickness has accumulated on the surface.

By means of the detection of the extent of the change of reflection ratios it is possible, for example, to detect the position changes or the appearance of an object, which moves or can be moved in front of the arrangement. If the change is a wetting, then concerted control commands can be derived, for example by means measuring of the quantity of the wetting liquid per unit of surface area and/or per unit of time on the wetted surface, by means of which, for example, the wetting can be regulated, closing events can be controlled as a function of the existing or expected quantity of liquid or an operation for removing the wetting can be optimally controlled as a function of the history of the cause of the wetting.

SUMMARY OF THE INVENTION

The object of the invention is to develop an arrangement of the type mentioned at the outset in such a way that an additional external radiation, which penetrates the arrangement from the area surrounding the arrangement for measuring or detecting a change, and is superimposed on the radiation of the arrangement, does not essentially affect, interfere with or distort the measurement or detection of the change, even if the additional external radiation constitutes an essential percentage or even a predominant portion in comparison to the radiation emitted for the measurement or detection.

The above object is attained by an arrangement for indicating a change in a reflective element of a radiation-permeable medium having a detection side disposed opposite the reflective element. The arrangement includes two measured sections for generating, reflecting and receiving radiation for measurement, each having a radiation source disposed adjacent the detection side of the medium for generating radiation for transmission through the radiation-permeable medium thereby resulting in generated radiation; a sensor-active surface on the reflective element for reflecting at least a portion of the generated radiation thereby resulting in reflected radiation emerging from the detection side of the medium; and a radiation receiver disposed adjacent the detection side of the medium at a distance from the radiation source for receiving the reflected radiation, the radiation receiver having an output for producing a detection signal representing received radiation. The arrangement further includes a switch arrangement for periodically actuating respective ones of the measured sections in a successive, repeating switching sequence according to a predetermined switching sequence frequency, wherein the detection signal includes a modulation frequency corresponding to the predetermined switching sequence frequency; an adjusting device for adjusting the detection signal so that, in a rest state of the sensor-active surface of each measured section, a part of the detection signal corresponding to each measured section has an average amplitude value equal to an average amplitude value of parts of the detection signal corresponding to other ones of the measured sections; a filter circuit connected to the radiation receiver of each measured section for producing a filtered detection signal; and an evaluation device having an input for receiving the filtered detection signal and producing an output signal in dependence of a difference between parts of the filtered detection signal corresponding to respective ones of the measured sections.

In the case of wetting of an outer surface of a plate or wall, the radiation for measuring or detecting a change in a reflective element thus penetrates both the plate or wall and the liquid wetting the plate or wall without essential attenuation and an increasingly larger percentage of the radiation, which is emitted into the plate or wall at an angle of reflection which increases toward the perpendicular by means of the plate or wall, is reflected by the boundary of the outer surface of the plate or wall up to a limit angle of the angle of arrival, from which, at this surface, a total reflection of the radiation radiated occurs at an optically flawless boundary.

In this manner, a curve of the radiation intensity of a radiation flux, which emerges from the inner surface of the plate or wall to which the radiation source is coupled, is produced in a plane, which passes perpendicularly through the plate or wall at the location of the radiation source, as a function of the directional characteristic curve of the radiation intensity of the radiation source coupled to the plate or wall and of the attenuation of the radiation flux in the plate or wall. Between the coupling location of the radiation source and the radiation area of the total reflected radiation below the limit angle, this radiation flux curve has a generally wide maximum. The greatest change of the radiation intensity curve is to be expected at this maximum if the reflection of the radiation transmitted into the plate or wall at its wettable surface is changed as a result of wetting in a sensor-active area of the outer surface of the plate or wall, which area is disposed between this maximum and the coupling of the radiation source to the inner surface. In this connection, both the position and the height of this maximum change according to the kind of wetting of the outer surface of the plate or wall in the sensor-active area, which when dry, essentially contributes to the formation of this maximum of the radiation intensity on the inner surface of the plate or wall. In principle, a plurality of local maxima can be formed. For example, a luminous radiation in the visible, ultraviolet, or infrared range, an ultrasonic radiation or, if need be, capacitive radiations can be considered as a radiation which passes through both the wetted plate or wall and the wetting fluid.

However, the radiation-permeable medium need not be a plate or wall. In a different radiation-permeable medium, for example the air, the arrangement can detect changes in the reflection ratios, as long as measured sections between the arrangement, which usually includes radiation source and radiation receiver, and a reflecting element, for example a mirror or a hand, can be provided. Reflected stray light alone permits the arrangement to detect position changes or the approach of a hand, for example.

The arrangement of at least two measured sections, no matter whether two radiation sources or groups of radiation sources are associated with one radiation receiver or whether a plurality of radiation receivers are associated with one radiation source, and the arrangement of each radiation receiver in the zone of the maximum of each radiation flux distribution of the radiation source(s) coupled to the plate or wall, which radiation flux distribution emerges from the inner surface of the plate or wall, the alternating and successive actuation of the measured sections in a particular revolving switching sequence, the adjustment of the radiation output of the radiation sources or groups of radiation sources to such a value that the detection signal at the output of the radiation receiver is unchanged in the output or state of rest of the reflective element in the revolution of a switching sequence for the actuation of the individual radiation sources or groups of radiation sources, and the type of exploitation of the difference of the parts of the detection signal associated with the individual radiation sources or groups of radiation sources when there is a change of the reflection ratios, for example as a result of wetting in the sensor-active area, all result in the advantage that the arrangement detects a very wide range of a change, for example as a result of the wetting of the plate or wall, and that a direct external radiation on the radiation receiver has virtually no effect on the evaluation of the active radiation emitted for the measurement or detection, even if the intensity of the external radiation is essentially many times greater than the intensity of the active radiation, and that because of the embodiment of the arrangement in a manner according to the invention, the external radiation does not affect the active radiation as a result of the changes, for example the changes brought about by wetting.

The reliability of the detection of change is increased further by the fact that a switching sequence frequency of the switching sequence for the alternating actuation of the radiation sources or groups of radiation sources associated with a radiation receiver is chosen, which frequency is essentially many times greater than the fastest expected change sequence of an external radiation acting upon the radiation receiver, and that only that detection signal is evaluated whose change sequence has the same sequence frequency as the switching sequence.

Further advantageous embodiments of the invention are recited in additional dependent claims.

BRIEF DESCRIPTION OF THE DRAWINGS

The invention will be described in detail below by means of advantageous exemplary embodiments. Shown in the associated drawings are in:

FIG. 1b, a diagram with a curve depicting the radiation intensity of the reflection of the arrangement shown in FIG. 1a;

DETAILED DESCRIPTION OF THE PREFERRED EMBODIMENTS OF THE INVENTION

The description is given in connection with the example of an arrangement for measuring and detecting wetting, although the arrangement can also detect other changes of the reflection ratios in comparison to a stationary or output state, which changes are not caused by wetting. Considerations in this connection concern for example the detection of position changes or the approach of an element, which possibly only reflects stray light, if for example particular reactions are intended to occur as a function of the approach of a hand to a mirror. In the exemplary embodiments, the radiation-permeable medium is a plate or wall 1, but other radiation-permeable media, for example bodiless ones, can also be used, wherein the changes are caused by an insertion of a medium into the beam path of the measuring device or by its movement in the beam path, which medium reflects the active radiation of the radiation sources and makes possible the construction of measured sections.

Figure 1A:
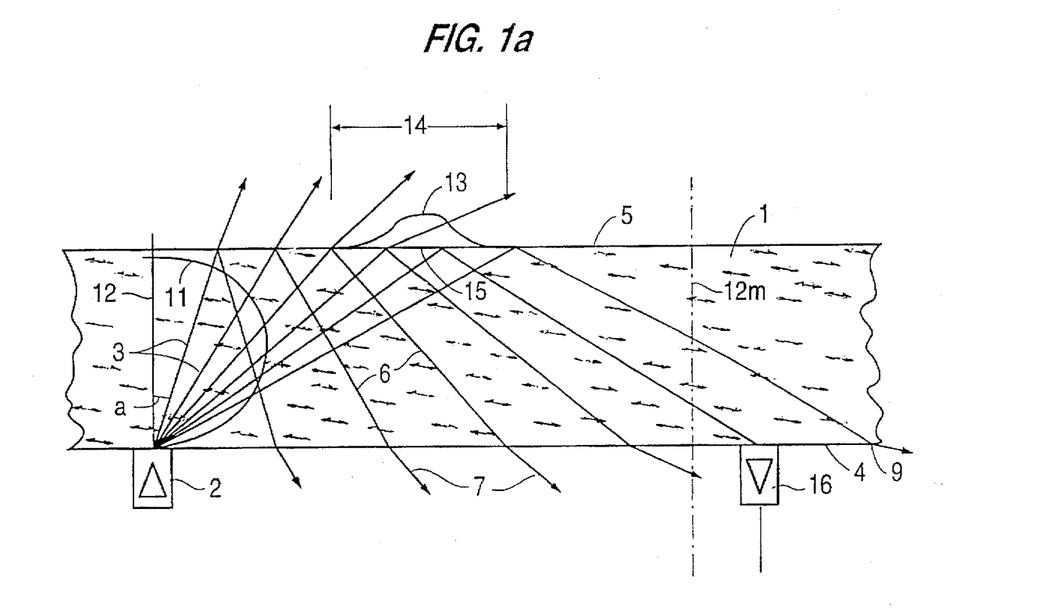
FIG. 1a, a vertical section through a radiation-permeable plate or wall with a switching source coupled thereto.
Figure 1B:
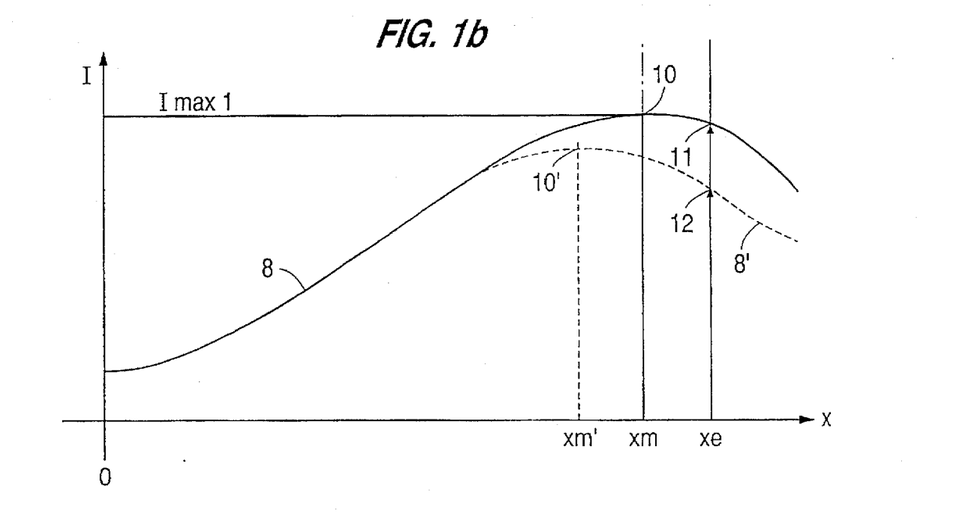

FIG. 1a shows a vertical cross section of a plate or wall 1. The plane runs perpendicular to the plate through a radiation source 2 which is coupled to the plate or wall and whose radiation into the plate is shown by lines 3. The radiation source is coupled to the inner surface 4 of the plate 1 so that the radiation 3 generated by it can flow in essentially without losses. At the outer surface 5 of the plate 1, which is disposed opposite the inner surface 4 of the plate, this radiation is reflected in accordance with the laws of optics by a portion of the outer surface. The reflected radiation increases with the increasing angle of incidence a (reflected radiation 6) and partially re-emerges at the inner surface 4 of the plate or wall as reflective radiation 7. The radiation intensity course I of this reflection 7 as a function of the distance x from the radiation source is schematically represented as curve 8 in the diagram of FIG. 1b. In the area covered by the distance between the radiation source 2 and the emergence 9 of the reflection of the first total reflection at the inner surface 4 of the plate, this curve has for example a first maximum 10, which essentially depends on the radiation characteristic curve of the radiation source 2 in the plate 1. In this respect, a plurality of maxima can also easily be detected and evaluated in the signal curve. In FIG. 1a, this radiation characteristic curve is schematically represented as curve 11 and schematically indicates the angle-dependent radiation intensity of the radiation source in the plate.

If wetting of the outer surface 5 of the plate or wall occurs in a particularly sensitive area of the outer surface between a perpendicular 12 to the plate at the location of the radiation source and a perpendicular 12 m through the plate at the location xm of the first maximum, namely in the sensor-active area 14 of the plate or wall, in which area the reflection for the maximum 10 is reflected by the outer surface, which wetting is schematically represented in FIG. 1a by a drop in this sensor-active area or surface 14,then optical reflection system on the outer surface in the support area 15 of the drop 13 changes in such a way that as a result of the changed reflection the shape of the radiation intensity curve 8 of the reflection 7 changes into the curve 8' which is changed by the wetting, and the position xm of the maximum 10 changes into the new position xm' of the maximum 10' of the changed curve 8'.

If a radiation receiver 16, which is shown in FIG. 1a is coupled to the inner surface 4 of the plate or wall 1 in the area of the maximum 10 of the radiation intensity of the reflection 7, for example at a distance xe from the coupling point of the radiation source 2, then this radiation receiver 16 receives a radiation intensity I1 of the reflection 7 determined by the curve 8, via the measured section when the sensor-active area 14 of the plate is dry; in the event that the sensor-active area of the plate is wet, receiver 16 receives a radiation intensity I 2 of the radiation curve 8' of the reflection of the plate, which reflection has been changed as a result of the wetting. The change of the radiation intensity of I1 to I2 indicates the wetting of the sensor-active area 14 of the plate or wall 1.

Figure 2:
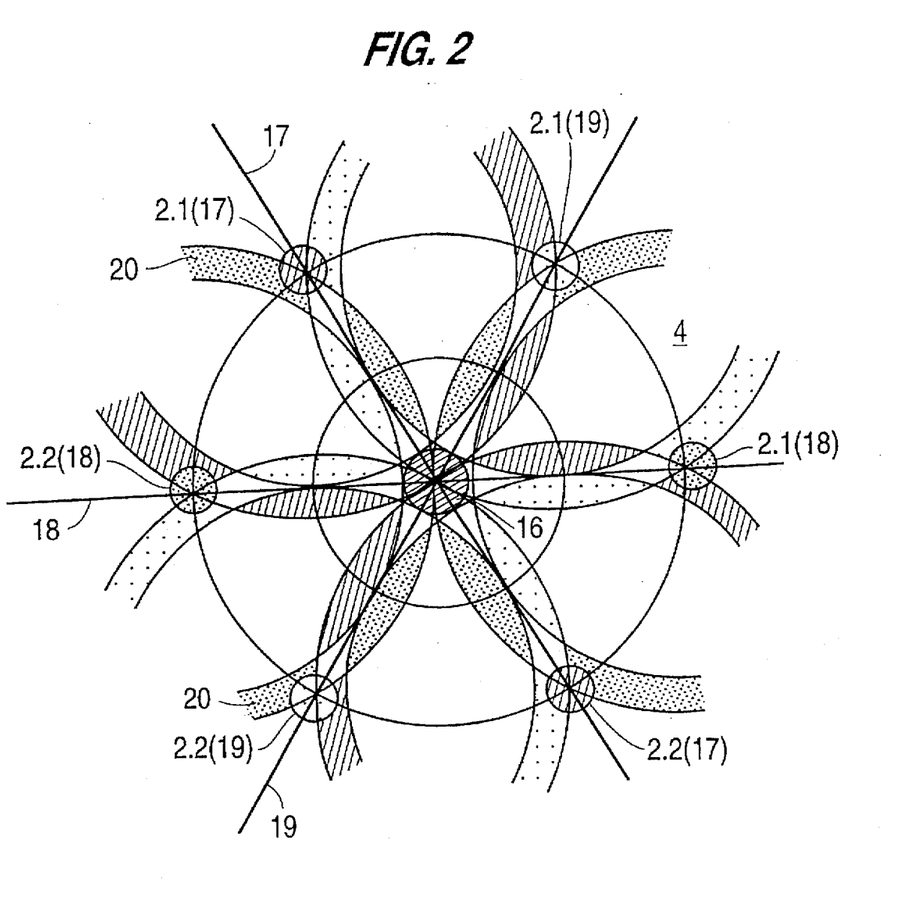
FIG. 2, a detail of the inner surface of a wettable plate or wall having mounted radiation sources and a radiation receiver.

FIG. 2 shows the inner surface 4 of a wettable plate or wall 1 with three groups 17, 18, and 19 each with two radiation sources coupled in pairs to the inner surface, namely the radiation sources 2.1 (17), 2.2 (17) of the first group 17, the radiation sources 2.1 (18), 2.2 (18) of the second group 18, and the radiation sources 2.1 (19), 2.2 (19) of the third group 19, which are all associated with a common radiation receiver 16 and which are disposed in a circle around the common radiation receiver 16 so that the radiation receiver is disposed on the approximately annular zone 20 of the maximum 10 of the radiation intensity of the reflection of the individual radiation sources 2.1 (17) to 2.2 (19).

In the exemplary embodiment shown, respectively two radiation sources disposed on the side opposite the radiation receiver, constitute a group of two radiation sources. Naturally other arrangements are also conceivable in which a plurality of radiation receivers are disposed in a circle around one radiation source, provided that only two measured sections can be inquired and settled independently of each other.

Figure 3:
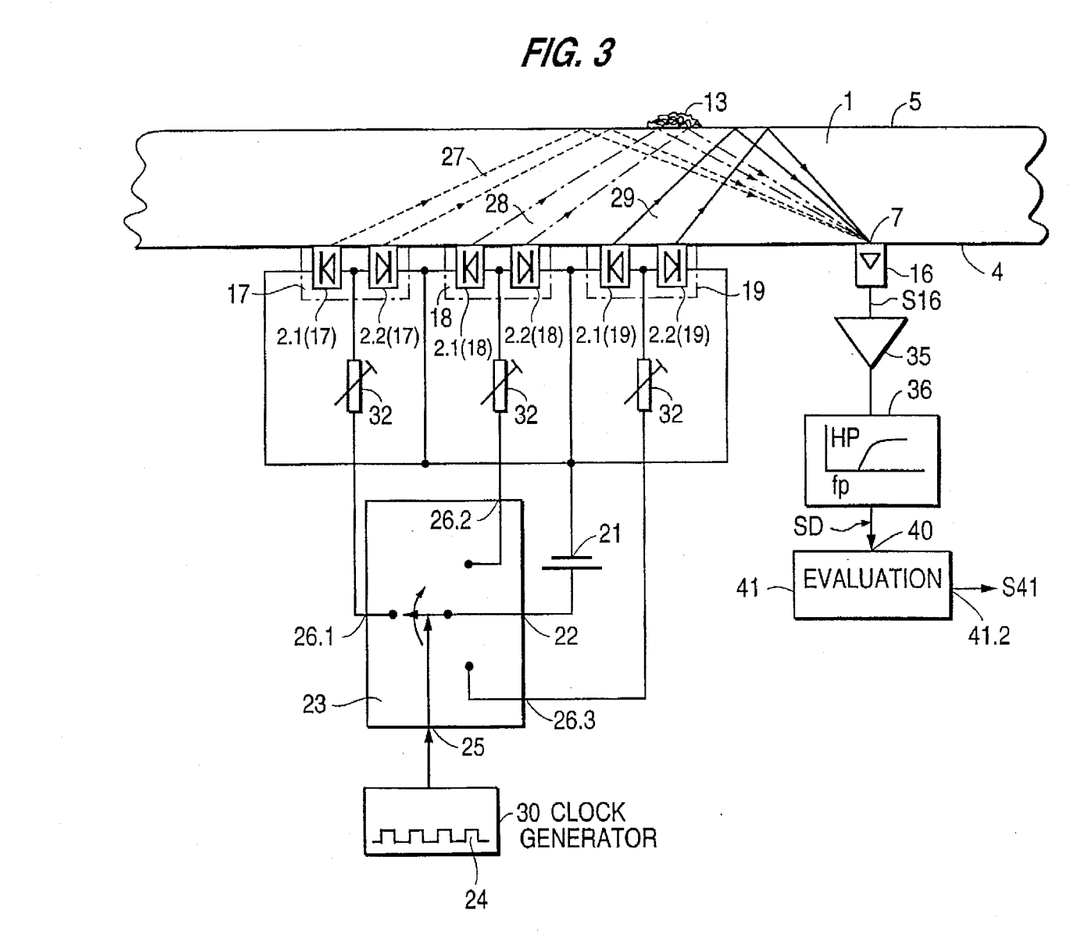
FIG. 3, a block circuit diagram of an arrangement for measuring or detecting wetting, together with an arrangement as shown in FIG. 1 of the sensor-active area of a plate wall, FIGS. 4a–4d, the chronological course of the output signals of the radiation receiver and of the detection signal, FIG. 5, a block circuit diagram of a different arrangement for measuring or detecting wetting of a plate or wall with two particularly coupled radiation sources and a regulating arrangement.

The operation of the arrangement, shown in FIG. 2, of three groups of radiation sources around an affiliated radiation receiver is explained in detail by means of a circuit arrangement, an exemplary embodiment of which is shown in FIG. 3. FIG. 3 schematically represents a vertical section of a detail of a wettable plate 1 or wall with the six radiation sources 2.1 (17) to 2.2 (19), schematically represented in FIG. 2. The radiation sources are coupled to the inner surface 4 of the plate 1. The affiliated radiation receiver 16 is likewise coupled to the inner surface. In the exemplary embodiment shown, the radiation sources are light-emitting diodes, whose one terminal is connected to the one pole of a current source 21. The other pole of the current source is connected to the input 22 of a three-position sequence switch 23, which connects the signal input 22 to the next signal output 26.1, 26.2, or 26.3 at its control input 25 after each control pulse 24. In the exemplary embodiment shown, in which the signal input is connected to the signal output 26.1, the signal input is connected to the subsequent signal output 26.2 by means of the next control pulse. As a result, the radiation source groups 17, 18, and 19 are alternatingly connected to the current source 21 one after the other through the switching sequence of the switching sequence frequency fa of the pulse generator 30, which is connected to the control input 25 of the sequence Switch 23, so that the radiation source groups 17, 18, and 19 are alternatingly actuated one after the other until the following group is switched on.

Figure 4A:
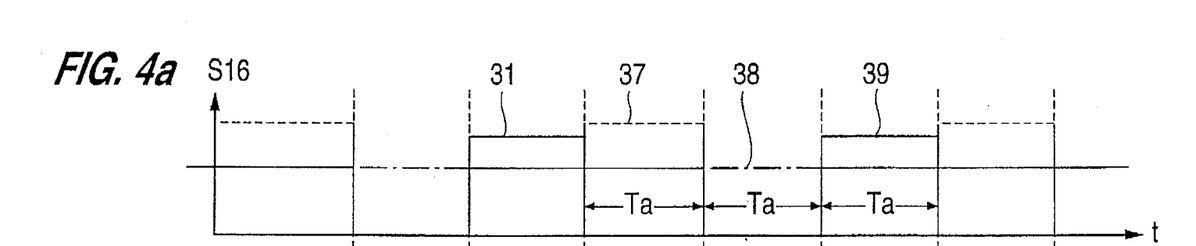

The course of the radiation of the individual radiation source groups in the radiation-permeable plate 1 is schematically indicated in FIG. 3 by the variously structured lines 27, 28, and 29. The portion reflected on the outer surface 5 of the plate partially emerges again from the inner surface 4 of the plate as reflection 7. The radiation receiver 16 coupled to the inner surface of the plate 1 in the zone of the radiation intensity maximum of the reflection, which is a photo element in the exemplary embodiment shown, converts the received radiation flux into an electrical output signal S 16, whose chronological course 31 is schematically represented over a time axis t FIG. 4a. Output signal S 16 is constituted of repeating signal parts 37, 38, 39, which are strung one after the other. These signal parts are produced from the same switching sequence, according to which the individual groups 17, 18, and 19 of radiation sources are switched on and off again to emit a luminous radiation for a short time interval Ta, which is equal to the period of time of the pulse frequency fa of the pulse generator 30 Controlling the sequence switch 23.

Figure 4B:
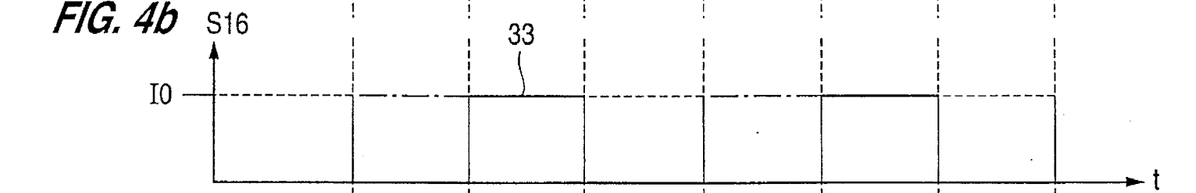
Figure 4C:
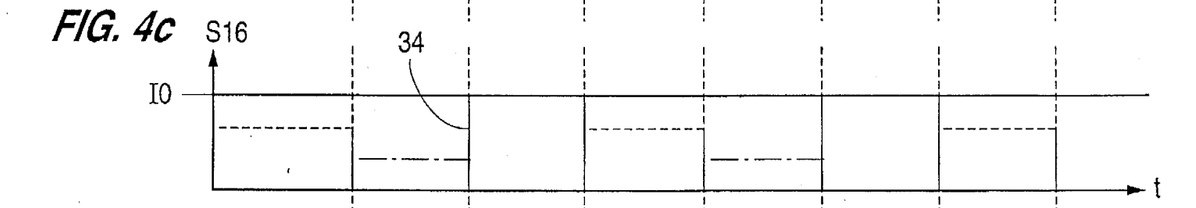
Figure 4D:
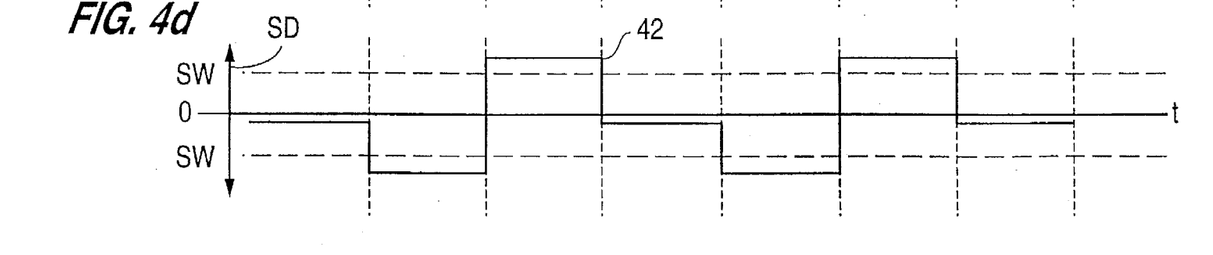

Adjusting members 32 of the signal outputs 26.1 to 26.3 of the sequence switch 23, serve to adjust the radiation output of the individual groups 17, 18, and 19 of the radiation sources so that when the plate or wall 1 is dry and undisturbed, each group of radiation sources generates for itself the same compensation value I0 of the output signal S 16 of the radiation receiver, as is schematically represented in FIG. 4b, at a chronological course 33 of the undisturbed and balanced output signal S 16 of the radiation receiver 16. If the sensor-active area 14 of the plate 1 is wetted, for example by a drop 13 as schematically represented in FIG. 3, the radiation route 27, 28, 29 is changed by this wetting in such a way that the radiation flux portions of the individual radiation source groups 17, 18, and 19 displace their portions to the balanced course 33 of the output signal S 16, so that for example a chronologically smooth course 34 of the output signal S 16 of the radiation receiver 16 is produced, which is shown in FIG. 4c. This output signal S 16 reaches the signal input 40 of an evaluation device 41 as a detection signal SD via an amplifier 35 and a high-pass filter 36. The limiting frequency fp of the high-pass filter 36 is calculated so that, on the one hand, the course 34 of the output signal S 16 which, when there is wetting to be detected or measured, is constituted by the individual parts 37, 38, and 39 of the sensor-active area of the plate or wall 1, is approximately transmitted further by the filter, and that on the other hand, fluctuations from external radiations on the radiation receiver 16, which likewise converts these into electrical signals, are no longer effective in the detection signal SD. This chronological course of the detection signal SD produced at the output of the high-pass filter 36 is schematically represented in a solid, unbroken curve 42 in FIG. 4d. In the exemplary embodiment shown, the evaluation device 41 includes a threshold circuit, not shown in detail, which generates a control signal S 41 at the output 41.2 of the evaluation device 41 when the course 42 of the detection signal SD exceeds a particular threshold value SW. This control signal S 41, not shown in detail, indicates wetting of the wetted plate 1 or wall in the sensor-active area 14 of the plate and can be used to control events which are dependent upon the wetting.

Figure 5:
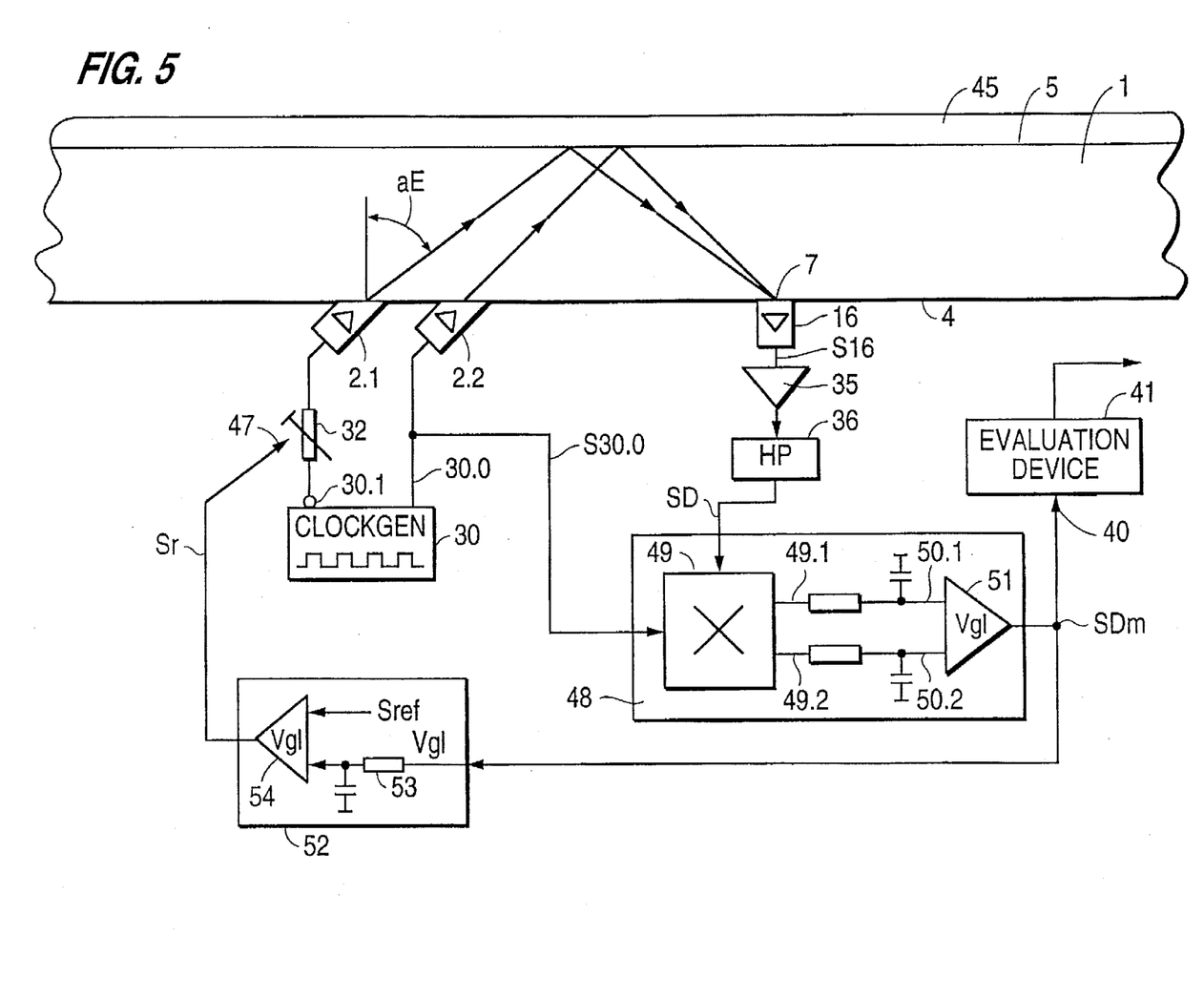

FIG. 5 shows a block circuit diagram of a different exemplary embodiment of an arrangement for measuring or detecting wetting of a plate 1 or wall, which wetting differs from the exemplary embodiment shown in FIG. 3 essentially because of the type of arrangement of the radiation sources in the sensor-active area 14 of the plate or wall and because of an additional regulating device for regulating the balancing of the radiant power of the radiation sources.

The two radiation sources 2.1 and 2.2 are coupled to the inner surface 4 of the plate 1 so that the angle of incidence aE of the maximum radiation intensity of a radiation source 2.1 or 2.2 in the plate or wall is approximately equal to the angle for which the maximum 10 of the reflection 7 from the inner surface 4 of the plate or wall reaches its greatest value in a plane which passes perpendicularly through the plate or wall at the location of the radiation source and of the affiliated radiation receiver 16, likewise coupled to the inner surface. As a result, a pronounced first maximum 10.1 of the radiation intensity curve 8.1 or 8.2 of the reflection 7 of the radiation sources is achieved from the inner surface 4 of the plate or wall 1, as schematically represented by means of the curves 8.1 and 8.2 of the radiation intensities I1 of the reflection of the radiation sources 2.1 and 2.2 shown in FIG. 6. The more pronounced the maximum of the radiation intensity curve of the radiation flux of a radiation source can be embodied, which flux emerges from the inner surface of the plate or wall, the more precisely and reliably wetting of the plate or wall can be detected and measured. Therefore, it is particularly advantageous to couple the radiation sources associated with a radiation receiver to the inner surface of the plate or wall, even if a measurement takes place only after a plurality of reflections. Furthermore, if the two radiation sources 2.1 and 2.2 are spaced apart from their affiliated radiation receiver at different distances x1 and x2, namely in such a way that when the two radiation sources are in a balanced state and when the plate or wall is dry, the radiation receiver 16 is disposed on the trailing edge 43 of the first maximum 10.1 of the reflection curve 8.1 of the first radiation source 2.1 and at the same time is disposed on the leading edge 44 of the first maximum of curve 8.2 of the reflection from the inner surface 4 of the plate or wall 1, which reflection is generated by the second radiation source 2.2. The above arrangement increases the precision and reliability of the detection and measurement of the wetting of a plate or wall, since when the sensor-active area of the plate or wall is wetted, the maximum changes not only in level, but also in the distance from the affiliated radiation source. Therefore even small changes in wetting are clearly detected by means of the position change of the maximum.

Figure 6:
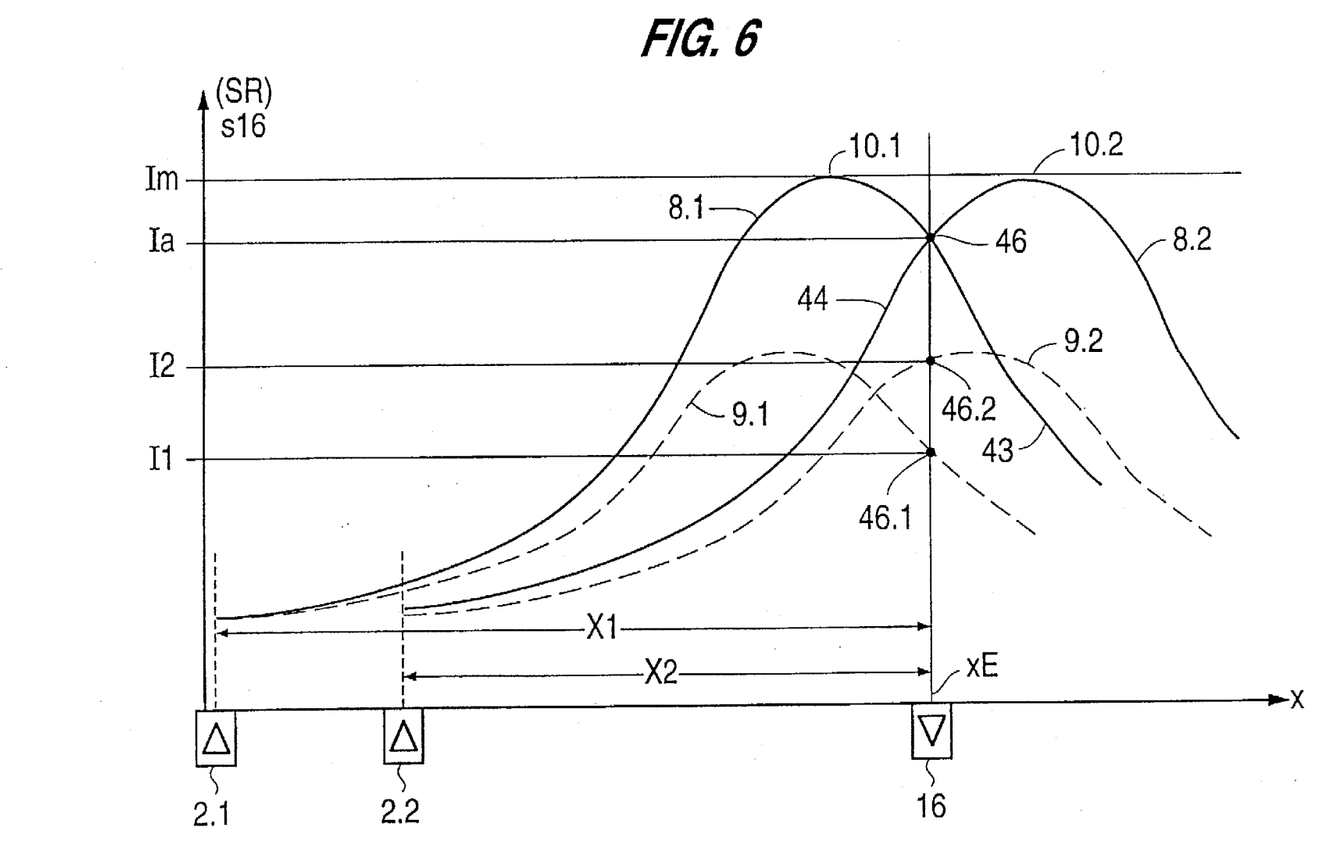
FIG. 6, diagram of the course of the radiation intensity curves of the reflection at the inner surface of the plate or wall when there is a particular coupling of two radiation sources on this surface.

With this arrangement of radiation sources 2.1 and 2.2, it is possible to detect or measure wetting in the form of a uniform liquid film or a uniform layer of liquid 45, as is schematically represented in FIG. 5 on the outer surface 5 of a plate or wall. As a result of the wetting, the edges 43 and 44 of the two curves 8.1 and 8.2 of the radiation intensity of the reflection for the dry plate are deformed and displaced in such a way that the balancing point 46, common to both curves, of the output signal S16 of the radiation receiver splits the two curves in two curve points 46.1 and 46.2 with two different amplitude values I 46.1 and I 46.2, as shown in FIG. 6, so that a signal difference of the detection signal SD can be derived from the above split to constitute a control and/or measurement signal S 41.

In the arrangement shown in FIG. 5, the switch arrangement to control the two radiation sources 2.1 and 2.2 is a pulse generator 30, which generates a current pulse alternatingly at a non-inverting output 30.0 and at an inverting output 30.1 for exciting the emission of the radiation source, which is connected to the output, for the duration of the current pulse. To adjust the current value, the one output of the current pulse generator 30 includes a current adjusting member 32, which can be adjusted by means of an adjustment signal Sr at its adjustment input The reflection of these two radiation sources at the coupling point XE (FIG. 6) of the radiation receiver 16 is converted by the adjustment signal Sr intop an electrical output signal S 16, which reaches the output of the filter circuit 36 as a detection signal SD via an amplifier 35 and a high-pass or band-pass 36 in accordance with the arrangement shown in FIG. 5 A signal centering stage 48 is connected to the output of the filter circuit 36, which stage impresses the changes of the detection signal SD on the output of the filter circuit 36 of a midrange voltage Uz. In the exemplary embodiment shown, the signal centering stage 48 includes a synchronous demodulator 49 with two demodulator outputs 49.1 and 49.2, each of which is associated with a radiation source. The association is carried out via a control pulse S 30.0 of the current pulse generator 30, which also controls the emission of the radiation sources. In the exemplary embodiment shown, the demodulator outputs 49.1 and 49.2 are followed by demodulation value memories 50.1 and 50.2 which momentarily store the average amplitude value of the signal parts of the demodulation signal SD, which parts are scanned by the synchronous demodulator 49 and are associated with both radiation sources, and in this manner constitute an envelope demodulator. The difference value is produced from the momentary, average amplitude values of the two detection value memories in an adjoining operational amplifier 51 and impressed on a mean value. The smoothed detection signal SD m produced in this way, which is essentially freed from interferences in comparison to the detection signal SD at the output of the filter circuit 36, is supplied to both an evaluation device 41 and a regulating circuit 52 with a high control time constant Tv. In the exemplary embodiment shown, the regulating circuit includes a time constant member 53 and a comparator 54, which produces an adjusting signal Sr for the adjusting input 47 of the current adjusting member 32 from the comparison with a reference signal Sref in such a way that the radiation output of the radiation source 2.1, which is regulated by means of the current adjusting member, is changed the difference of the detection amplitude values at the output of the signal centering stage 48 thereby approaching zero. The regulating speed, i.e. the control time constant Tv of the regulating circuit 52, is calculated in this connection so that it is essentially many times greater than the slowest changes of a wetting process to be detected.

On the input side, the evaluation device 41 can also be directly connected to the output of both detection value memories 50.1 and 50.2, in particular when the wetting is intended to be measured by means of measured by means of the evaluation device. The control time constant is essentially many times greater than an oscillation period of the switching sequence signal, which switches the radiation sources or groups of radiation sources associated with the radiation receiver. As a result, slower or lasting changes in the sensor-active area of the plate or wall, which were not caused by the wetting or do not concern it, are not taken into account when detecting or measuring the wetting, and influences, which result from change, dirt accumulation, or temperature differences and which cause problems for known systems, can be easily eliminated.

If desired, a plurality of radiation receivers, which are photodiodes in the example, and a plurality of radiation sources, which are LEDs in the example, can also be connected in series in order to increase the number of paths and hence to increase the reliability of the measurement results. For example, four LEDs can be disposed so that a photodiode is situated in the center of four LEDs disposed on the corners of a square. As a result, there are four measuring devices which are independent of one another. The above number can be easily increased in the event that increased reliability requirements are made on the arrangement. An embodiment with a plurality of radiation sources which are associated with a radiation receiver has the advantage over the inverse arrangement a (plurality of receivers—one source) that, for example in the control of windshield wiper motors in motor vehicles, the influence of external light, which interferes with only one part of the measured sections, can be better filtered out.

Figure 7:
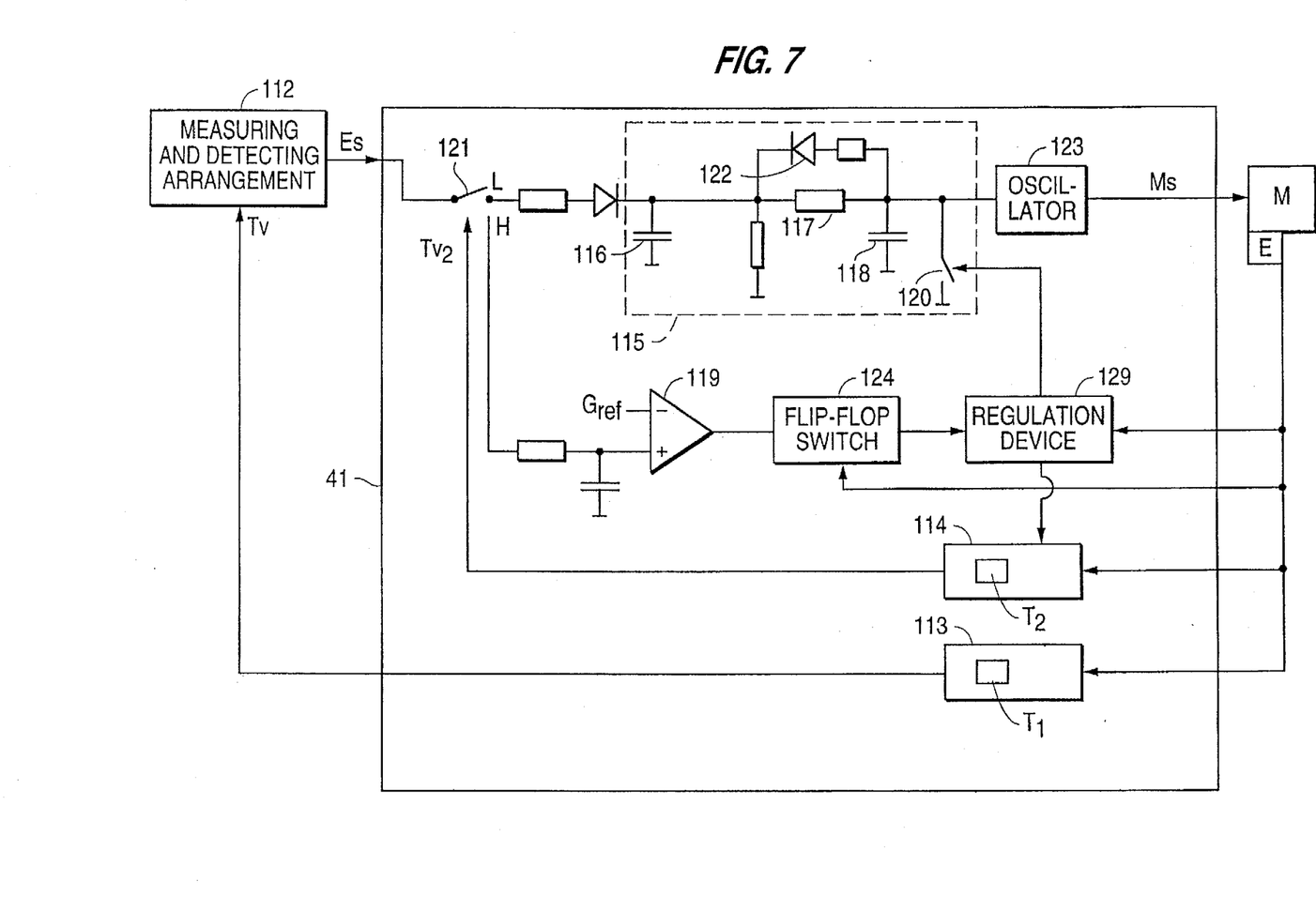
FIG. 7, a block circuit diagram of an evaluation device.
Figure 8:
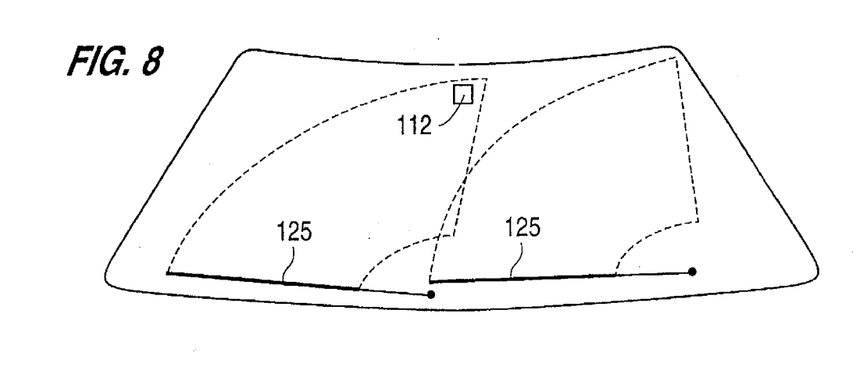
FIG. 8, a schematic representation of a windshield.

As soon as a device (windshield wiper, sprayer system) is controlled as a function of the wetting, the arrangement 112 in FIG. 7 can be made less sensitive so that further changes can be reliably detected. One need only consider streaks left behind by a windshield wiper, which at high sensitivity would lead to a signal, although they dry by themselves. Thus, for example at least while the removal device is sweeping across the measured sections, the time constant can be short so that the signal which is generated by the removal device is suppressed to a large extent or the evaluation device has a memory unit, which essentially stores the signals that occur as long as the time constant is set long and which at least partially blanks out the signals which occur while the removal device is sweeping across the measured sections when the time constant is short.

If need be, the evaluation device evaluates the signals, which are detected with regard to their intensity while a removal device is sweeping across the measured sections, and as soon as the intensity falls below an adjustable limit value, it clears a memory unit, whose contents govern the control of the removal device. As a result, the arrangement can react rapidly and flexibly, e.g. in a vehicle when the windshield wiper need be quickly returned to the state of rest because the vehicle stops at a light or enters a tunnel. In this connection, the signals which stem from the sweeping, that is primarily the signals produced by the sweeping, are integrated. If the detected value falls below a limit value, the reset is carried out.

Figure 9A:
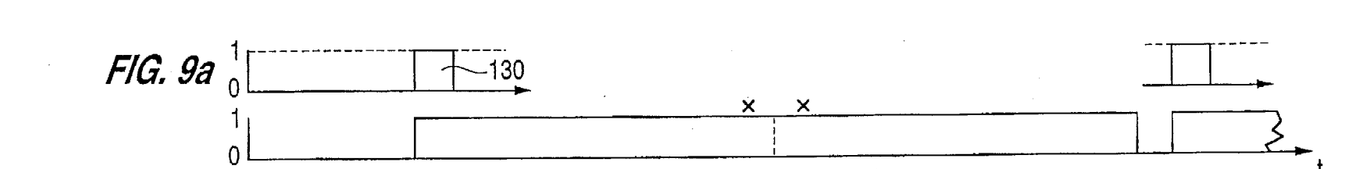
FIG. 9, diagrams a) to d) of the chronological course of the motor limit switch signals and of the motor; of the signal course when a little wet and when very wet; of the changing time constants, FIG. 10, a block circuit diagram of a different embodiment.
Figure 9B:
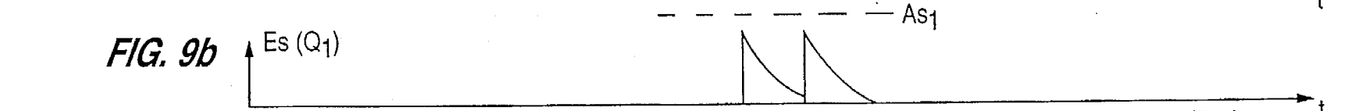
Figure 9C:
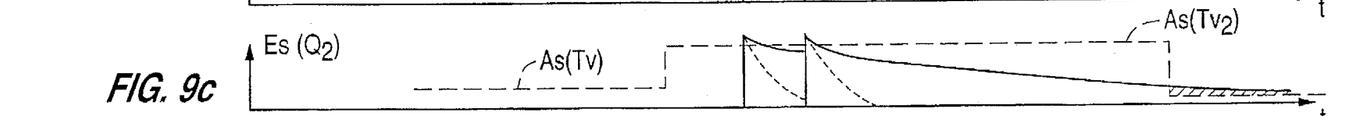
Figure 9D:
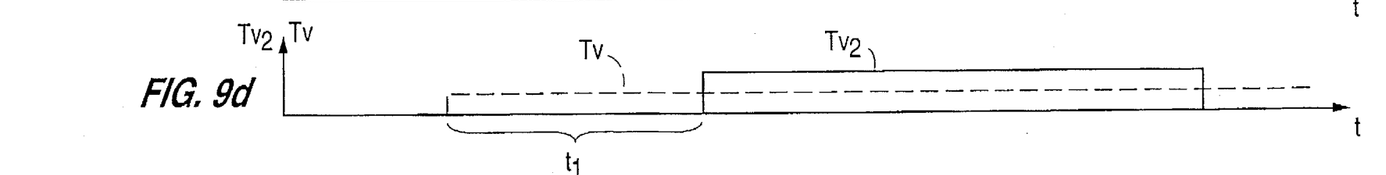

FIG. 9a shows the chronological course of a wiping event when a windshield according to FIG. 2 is swept by windshield wipers 125, wherein the windshield wiper at the positions x sweeps across the arrangement. The stream of water pushed in front of the windshield wipers 125 causes strong pulses and input signals Es (Q1) (e.g. water quantities Q1 in FIG. 9b). This signal can adulterate the results, but if the sensitivity at this point is reduced, then this signal cannot have any negative influence. The time constant can be changed, for example from Tv to Tv2, via adjusting means 114 or switching means 121, (FIG. 7). Alternatively, at a particular time t1 after the Start signal 130 of the wiper, a sensitivity change is produced, for example by means of timer T2 (FIG.7, FIG. 9d). Then the input signal Es (Q2) only slightly exceeds the threshold value As (Tv2), which is increased in relation to the threshold value As (Tv).

As further shown in FIG. 7a memory unit 115 includes a first memory 116, which sends its signals to another memory 118 via an attenuator 117 which is dependent upon a threshold value. Strong signals can be supplied directly to the other memory 118 by means of a bypass circuit 122. Depending upon the memory contents, a measurement value signal Ms is sent via oscillator 123 to the windshield wiper motor M, which can send signals for the adjusting means 113, 114 via its limit switch E. It is noted that the above connection to the limit switch is not absolutely required. Depending on signal intensity, the windshield wiper can alternatively be changed directly to continuous operation or even to the higher speed stage of the wiper motor.

The values determined while sweeping can be detected for evaluating a dry-running control. If for example a vehicle must come to a stop at a light or moves into a tunnel, the quantity of water to be removed is possibly reduced suddenly. The stream of water in the area of the windshield wiper 125 is reduced. If the signals occurring during sweeping are integrated by means of an integrator 119, a measure is produced for the stream of water. If the measurement value falls below a limit value G ref and for example the flip-flop switch 124 signals a further running of the wiper, switching means 120 unload the memory 118 upon indication of the regulation device 129. With each new start signal of the wiper, the flip-flop switch is reset. Dry running is prevented, however. For safety reasons the wiper will possibly have to be gradually slowed down to zero in downward steps.

From time to time, individual events can lead to an unwarranted triggering of the arrangement. With an arrangement disposed on a motor vehicle, this can for example occur when an insect strikes it or a similar one-time event occurs. An unintentional triggering of the windshield wiper can frighten the driver of the vehicle. Now the arrangement discerns whether this is a one-time event and enables the signal flow to the evaluation device 41 only after the occurrence of further signals.

Figure 10:
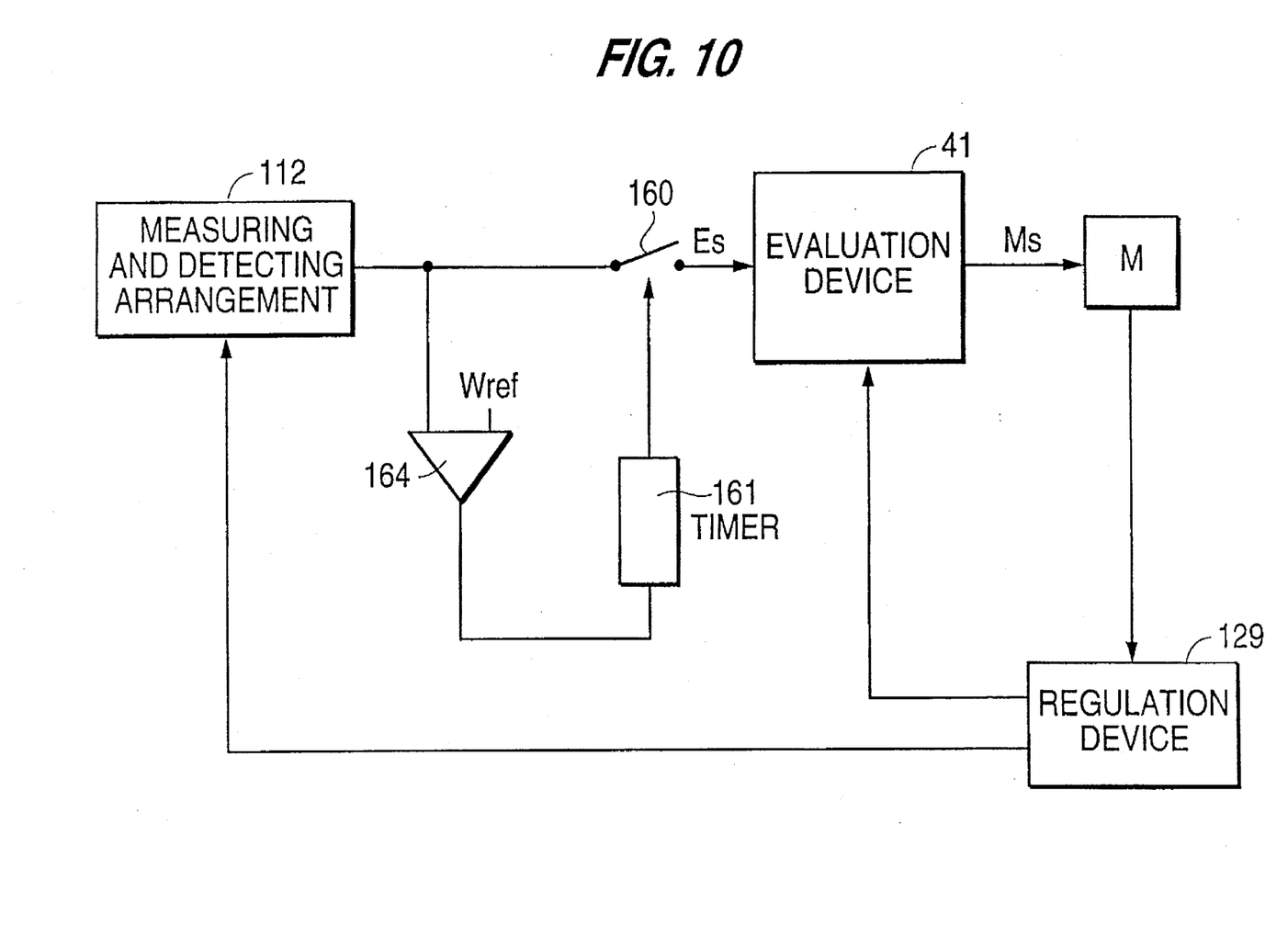

To this end, in FIG. 10 switching means 160, which are opened with a first signal, are connected upstream of the evaluation device 41. The first signal is carried to a threshold switch 164, which compares the signal to a reference signal Wref. If the signal is greater than the reference value, the switching means 160 are actuated via a timer 161, and the connection between arrangement and evaluation device 41 is only made by virture of the above. If the next input signal follows within the time predetermined by the timer 161, this next input signal reaches the evaluation device 41 directly, but also passes through the threshold switch 164. If the threshold value is exceeded once more, then the running time of the timer 161, which produces the temporary connection, is started again.

Figure 11:
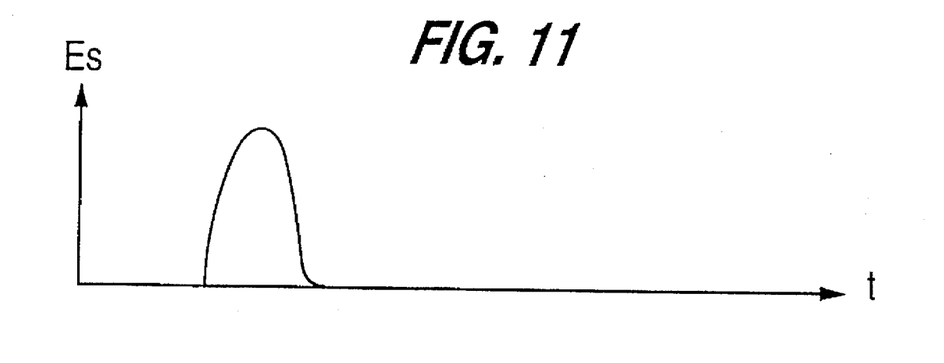
FIGS. 11 to 13, three examples of different input signals.
Figure 12:
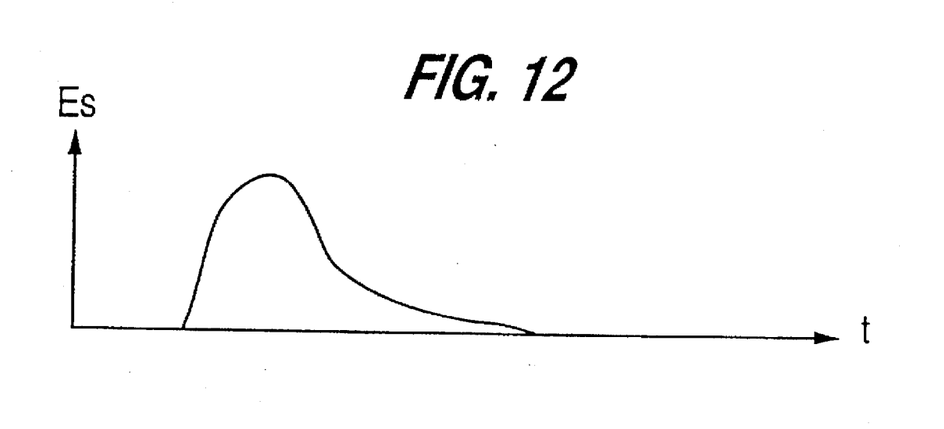
Figure 13:
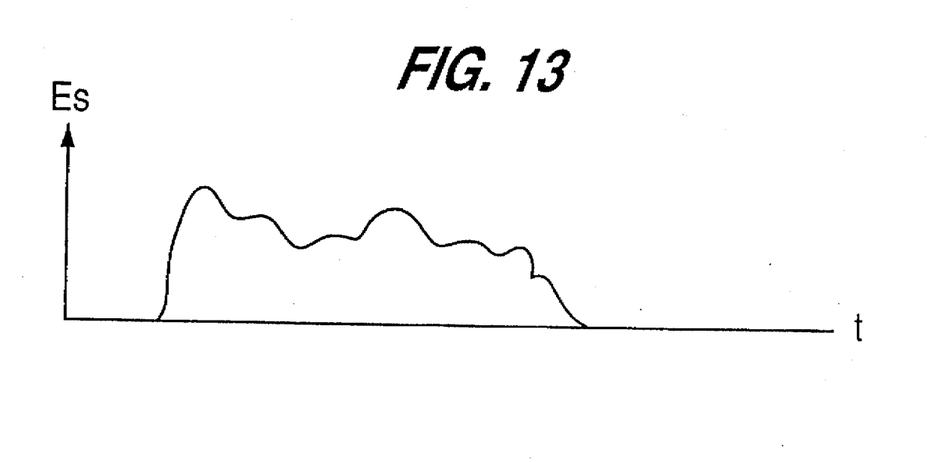

The different input signals can be inferred from FIGS. 11 to 13. When an insect strikes the windshield, an input signal Es is generated over the time t according to FIG. 11. The arrangement recognizes a one-time change, for which an correction is made. Since, however, no further signal occurs in the foreseeable time, there is no effect on the evaluation device 41.

When there is one drop of water according to FIG. 12, the arrangement corrects the change, but new changes are reported so that in comparison to FIG. 11, a slower tapering off is produced. At a corresponding signal reference value, the evaluation device starts the removal device. According to its signal course, this drop of water clearly differs from a drop according to FIG. 13, which is moved by the wind and which as a results of a plurality of signals can possibly trigger the removal device.

I claim:

1. An arrangement for indicating a change in a reflective element of a radiation-permeable medium having a detection side disposed opposite the reflective element, the arrangement comprising:

at least two measured sections for generating, reflecting and receiving radiation for measurement, each measured section including:

a radiation source disposed adjacent the detection side of the medium for generating radiation for transmission through the radiation-permeable medium thereby resulting in generated radiation;

a sensor-active surface on the reflective element for reflecting at least a portion of the generated radiation thereby resulting in reflected radiation emerging from the detection side of the medium; and a radiation receiver disposed adjacent the detection side of the medium at a distance from the radiation source for receiving the reflected radiation, the radiation receiver having an output for producing a detection signal representing received radiation;

a switch arrangement operatively coupled to the at least two measured sections for periodically actuating respective ones of the measured sections in a successive, repeating switching sequence according to a predetermined switching sequence frequency, wherein the detection signal includes a modulation frequency corresponding to the predetermined switching sequence frequency;

an adjusting device operatively coupled to the at least two measured sections for adjusting the detection signal so that, in a rest state of the sensor-active surface of each measured section, a part of the detection signal corresponding to each measured section has an average amplitude value equal to an average amplitude value of parts of the detection signal corresponding to other ones of the measured sections;

a filter circuit connected to the radiation receiver of each measured section for producing a filtered detection signal; and an evaluation device having an input for receiving the filtered detection signal and producing an output signal in dependence of a difference between parts of the filtered detection signal corresponding to respective ones of the at least two measured sections.

2. The arrangement according to claim 1, wherein:

the at least two measured sections comprise a first measured section and a second measured section including, respectively, a first radiation source and a second radiation source;

the switch arrangement is operatively connected to the first and second radiation sources; and the adjusting device is operatively connected to the first and second radiation sources for adjusting a radiation output of each of the first and second radiation sources so that, in the rest state of the sensor-active surface, each of the first and second radiation sources produces a part of the detection signal having an average amplitude value equal to an average amplitude value of parts of the detection signal produced by other ones of the first and second radiation sources.

3. The arrangement according to claim 2, wherein:

the first and second radiation sources are effective for generating radiation such that the reflected radiation corresponding to each of the first and second radiation sources exhibits a radiation strength curve reaching a maximum value in a respective maximum radiation zone at a predetermined distance from the respective radiation source on the detection side of the medium when the sensor-active surface is in a rest state, the first and second radiation sources thereby having respective maximum radiation zones; and the radiation receiver of each measured section is disposed in a zone of overlap of the maximum radiation zones.

4. The arrangement according to claim 1, wherein:

the medium is one of a plate and a wall;

the reflective element is a wettable outer surface of the medium; and the detection side of the reflective element is an inner surface of the medium disposed opposite the outer surface, the radiation sources being disposed to generate radiation toward the inner surface.

5. The arrangement according to claim 1, wherein the adjustment device includes:

a circuit arrangement having a current pulse generator generating a non-inverting output and an inverting output; and a current adjusting member disposed in at least one of the non-inverting output and the inverting output for adjusting a radiation output of a corresponding radiation source, the current adjusting member being adapted to be switched by at least one of the non-inverting output and the inverting output.

6. The arrangement according to claim 1, wherein the filter circuit includes a high-pass filter.

7. The arrangement according to claim 3, wherein:

the first and second radiation sources are disposed on the side of the medium opposite the reflective element at a distance relative to one another, the first and second radiation sources, and thus the first and second measured sections, sharing a common radiation receiver;

the maximum value on the radiation strength curve of the reflected radiation generated by the first radiation source when the sensor active area is in its rest state is a first maximum value;

the maximum value on the radiation strength curve of the reflected radiation generated by the second radiation source when the sensor active area is in its rest state is a second maximum value; and the common radiation receiver is disposed on the detection side of the medium at a location between the first maximum value and the second maximum value.

8. The arrangement according to claim 1, further comprising a regulating device including:

a signal centering stage disposed at an output of the filter circuit for receiving the filtered detection signal therefrom, the signal centering stage having:

a synchronous demodulator for scanning an amplitude value of parts of the detection signal corresponding to each actuated one of the measured sections;

a demodulation value memory operatively connected to the demodulator for storing average amplitude values of the parts scanned by the demodulator; and a comparing device operatively connected to the demodulation value memory for generating a difference value of the average amplitude values stored by the demodulation value memory; and a regulation signal generator connected to an output of the signal centering stage and including:

a time constant member generating a control time constant Tr many times greater than an oscillation period of the switching sequence frequency; and a regulation signal generator operatively connected to the time constant member for generating a regulation signal Sr from the difference value of the average amplitude values stored by the demodulation value memory, whereby the adjusting device is connected to the regulation signal generator for receiving the regulation signal therefrom, the regulation signal being effective for guiding an adjustment effected by the adjustment device such that the difference value of the average amplitude values approaches zero.

9. The arrangement according to claim 3, wherein the first and second radiation sources are disposed relative to the reflective element such that an angle of incidence of a beam of maximum radiation intensity of each of the first and second radiation sources relative to the reflective element is approximately equal to an angle of emergence of a corresponding reflected radiation from the detection side of the medium at a location on the detection side where the reflected radiation reaches its maximum value.

10. The arrangement according to claim 1, wherein the evaluation device is adapted to evaluate an intensity of the filtered detection signal while a removal device sweeps across the reflective element at the sensor-active surface of each measured section, and further includes a memory unit responsive to the intensity of the filtered detection signal falling below a threshold control value for controlling the removal device.

11. The arrangement according to claim 10, wherein the memory unit includes a switching means for resetting the removal device, and an adjusting means operatively connected to the switching means for adjusting a time constant of the arrangement to a value many times greater than an oscillation period of the switching sequence frequency.

12. The arrangement according to claim 1, further comprising a switching means disposed to receive the detection signal prior to the evaluation device for suppressing at least a first input detection signal for producing an initial signal connection to the evaluation device for subsequent detection signals.

13. The arrangement according to claim 12, further comprising a timer operatively connected to the switching means for producing the initial signal connection to the evaluation device for a predetermined time interval such that each subsequent signal restarts the time interval.

* * * * *